United States Patent [19]

Knapp, Jr. et al.

[11] Patent Number: 4,523,033

[45] Date of Patent: Jun. 11, 1985

[54] HEART TESTING COMPOUND

[75] Inventors: Furn F. Knapp, Jr., Oak Ridge; Mark M. Goodman, Knoxville, both of Tenn.

[73] Assignee: The United States of America as represented by the United States Department of Energy, Washington, D.C.

[21] Appl. No.: 509,077

[22] Filed: Jun. 29, 1983

[51] Int. Cl.$^3$ .............................................. C07C 57/30
[52] U.S. Cl. ................................................... 562/496
[58] Field of Search ......................................... 562/496

[56] References Cited

PUBLICATIONS

Goodman, Mark M. et al., J. Nucl. Med., 23 (10), 904–908, 1982.

Primary Examiner—Paul J. Killos
Attorney, Agent, or Firm—Katherine P. Lovingood; Stephen D. Hamel; Judson R. Hightower

[57] ABSTRACT

The compound 15-(p-[$^{125}$I]-iodophenyl)-6-tellurapentadecanoic acid is disclosed as a myocardial imaging agent having rapid and pronounced uptake, prolonged myocardial retention, and low in vivo deiodination.

1 Claim, No Drawings

HEART TESTING COMPOUND

BACKGROUND OF THE INVENTION

This invention, which resulted from a contract with the United States Department of Energy, relates to a compound for detecting and evaluating heart disease.

Radiohalogenated long-chain fatty acids have been evaluated heretofore for use in detecting changes in myocardial perfusion. The practical use of previously known compounds of this type for heart testing has been limited, however, because of their relatively short residence time in the myocardium and excessive accumulation in the blood of a subject tested therewith. In an article titled "Biochemical Concept and Synthesis of a Radioiodinated Phenylfatty Acid For In Vivo Metabolic Studies of the Myocardium", published in the European Journal of Nuclear Medicine, Volume 15, 1980, H. J. Machulla et al reported that the use of radioiodinated 15-(p-iodophenyl) pentadecanoic acid avoids the high concentration of radioactive iodide in the blood that is associated with the use of other radioiodinated long-chain fatty acids. It has been found, however, that washout of 15-(p-[$^{125}$I]iodophenyl) pentadecanoic acid from the myocardium is relatively rapid. In an article titled "Myocardial Imaging with 9-[Te-123m] Telluraheptadecanoic Acid", published in the Journal of Nuclear Medicine, Volume 22, Number 11, November 1981, Furn F. Knapp, Jr. et al reported that 9-[$^{123m}$Te] telluraheptadecanoic acid shows rapid uptake and prolonged retention in the myocardium.

SUMMARY OF THE INVENTION

It is an object of this invention to provide a new long-chain fatty acid compound for use in detecting and evaluating heart disease.

Another object of this invention is to provide a long-chain fatty acid compound which combines the advantageous properties of 15-(p-iodophenyl) pentadecanoic acid and 9-[Te-123m] telluraheptadecanoic acid for use as a myocardial imaging agent, namely, the advantages provided by the radioactive iodine moiety of 15-(p-iodophenyl) pentadecanoic acid and the rapid uptake and prolonged retention in the myocardium exhibited by 9-[Te-123m] telluraheptadecanoic acid.

These objects are attained by the preparation of the new compound 15-(p-[$^{125}$I]iodophenyl)-6-tellurapentadecanoic acid in accordance with techniques disclosed hereinafter.

DETAILED DESCRIPTION

As will be described in detail hereinafter, the compound 15-(p-[$^{125}$I]iodophenyl)-6-tellurapentadecanoic acid can be prepared by the steps represented in the following equations:

Step (1)

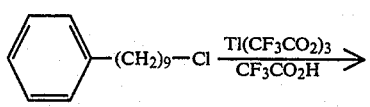

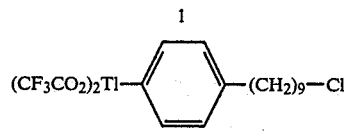

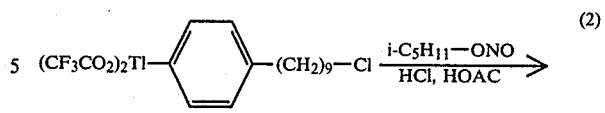

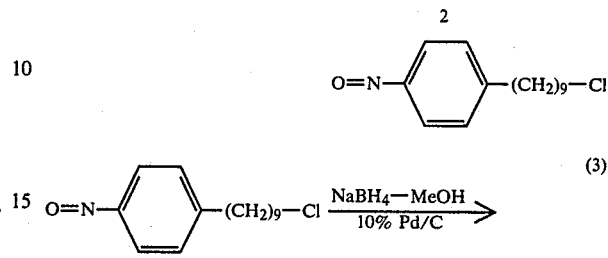

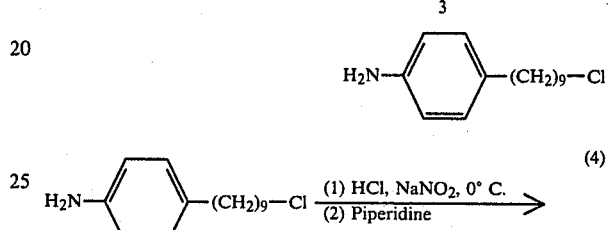

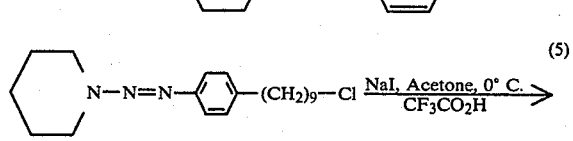

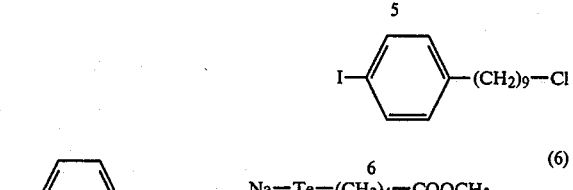

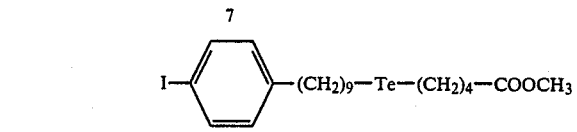

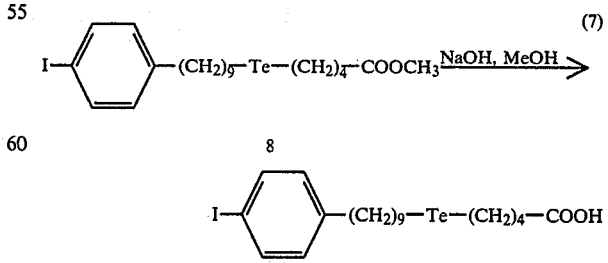

The following methods were employed in procedures reported herein. I-125 was obtained commercially. All solvents and chemicals were analytical grade and were used without further purification. Melting points of compounds were determined in capillary tubes by using a Buchi SP apparatus. The petroleum ether used for elutions was analytical grade and had a boiling range of 30°–60° C. Thin-layer chromatographic analysis (TLC) was performed by using 250-μm thick layers of silica gel G PF-254 coated on glass plates (obtained from Analtech, Inc.). Column chromatography was performed by using 60–200 mesh acidic or basic grade silicic acid (Sigma Chemical Co.). Infrared spectra (IR) were recorded on a Beckman 18-A spectrophotometer with NaCl plates or KBr pellets. Low-resolution mass spectra (MS) were recorded by using a Kratos MS-25 low-resolution instrument under the following conditions: ionizing energy, 70eV; accelerating potential, 8,000 V; trap current, 100 μA; probe temperature, 200°–300° C. Proton nuclear magnetic Resonance spectra ($^1$H NMR) were obtained at 60 MHz with a Varian 360-A instrument or at 200 MHz with a Nicolet high-resolution instrument. Samples (30–40 mg) were dissolved in deuteriochloroform (CDCl$_3$), and resonances reported downfield from the internal tetramethylsilane standard.

Step 1 illustrated above was conducted as follows:

A mixture of 1-chloro-9-phenylnonane (1.19 g, 5 mmol), thallium (III) trifluoroacetate (2.72 g, 5 mmol), and trifluoroacetic acid (5 ml) was protected from light and stirred at room temperature for 16 hours. The resulting dark green solution was vacuum distilled (0.6 mm, bath temperature 40° C.) followed by two vacuum codistillations with 1,2-dichloroethane to remove the excess trifluoroacetic acid. The amber oil remaining in the distillation flask consisted of 3.12 g (90%) of the crude 1-chloro-9[p-[bis(trifluoroacetyl)thallium]-phenyl] nonane (compound 1 above) which was used without further purification in the next step of the process.

In step 2 the thallium intermediate 1(3.12 g, 4.5 mmol) was stirred in CH$_2$Cl$_2$ (50 ml) at room temperature under red light with isoamyl nitrite (0.7 g, 6 mmol). A mixture of 12 N HCl (1.6 ml) and HOAc (2.4 ml) was then added and the solution was stirred 10 minutes. After the addition of 1.2 N HCl (20 ml), the solution was stirred an additional 10 minutes. The green mixture was washed several times with 0.1 N HCl and water and dried over anhydrous Na$_2$SO$_4$, and CH$_2$Cl$_2$ was removed in vacuo. The resulting green oil was chromatographed on a silicic acid (25 g). Fractions were eluted with petroleum ether (1–5) and 2% ether-petroleum ether (6–16 and 17–32). Fractions 17–32 were combined to give 0.83 g (70%) of 1-chloro-9-(p-nitrosophenyl) nonane (compound 2 above) as a green oil. Analysis by TLC (2% ether-petroleum ether) indicated the presence of the single nonane component.

In step 3 a mixture of the 1-chloro-9-(p-nitrosophenyl) nonane (1.0 g, 3.75 mmol) and 10% palladium on charcoal (50 mg) was stirred in MeOH (5 ml) at room temperature under argon. Following the addition of NaBH$_4$ (400 mg, 10 mmol) in MeOH (5 ml), the mixture was stirred 30 minutes. The yellow solution was then filtered into H$_2$O (50 ml) and extracted with Et$_2$O. The combined Et$_2$O extracts were washed thoroughly with H$_2$O and dried over anhydrous Na$_2$SO$_4$, and the solvent was removed in vacuo to yield 910 mg (97%) of the amine compound 3 (see step 3 above) as an orange oil (which was also analyzed by TLC).

The amine intermediate compound 3 was stirred in step 4, with 0.5 N HCl (4 ml) at 0°–5° C. Sodium nitrite (69 mg, 1 mmol) in H$_2$O (1 ml) was added dropwise to the mixture, which was then stirred at 0°–5° C. for 5 minutes. Piperidine (403 mg, 4.5 mmol) in H$_2$O (3 ml) was then added dropwise while the temperature of the reaction mixture was maintained at 0°–5° C. The solution was stirred at 0°–5° C. for 30 minutes, poured into H$_2$O (50 ml), and extracted several times with CH$_2$Cl$_2$. The combined organic extracts were washed thoroughly with H$_2$O and dried over anhydrous Na$_2$SO$_4$, and the solvent was removed in vacuo. The crude product was dissolved in benzene (2 ml) and chromatographed on silicic acid (basic, 25 g) slurried in petroleum ether. Elution with 2% ether-ether petroleum gave 1-[4-(9-chlorononyl)phenyl]-3,3-(1,5-pentanediyl) triazene (compound 4 above) in fractions 8–13 (143 mg, 41%) as an orange oil, this compound being analyzed by TLC.

In step 5, the triazene intermediate compound 4 (20 mg, 0.06 mmol) was dissolved in acetone (2 ml) and added dropwise to a mixture of triafluoroacetic acid (70 mg, 0.6 mmol) and sodium [$^{125}$I] iodide (4.68 mCi, 7.5 mg, 0.05 mmol) at 0°–5° C. The mixture was stirred at the same temperature for 5 minutes, diluted with H$_2$O, and extracted three times with ether. The combined ether extracts were washed thoroughly with H$_2$O, dried over anhydrous Na$_2$SO$_4$, and the solvent removed under a stream of argon. The resulting oily residue was dissolved in 2 ml of petroleum ether and applied to a silicic acid column (acidic grade, 2 cm I.D.) in a petroleum ether slurry. Fractions 20 ml in volume were eluted with petroleum ether and aliquots were taken for counting and TLC analysis. Fractions 14–20 were combined to give 1.17 mCi (25%) of 1-chloro-9 (p-[$^{125}$I] iodophenyl) nonane, compound 5 above. The produced showed a single radioactive component that co-chromatographed with unlabeled 1-chloro-9-(p-iodophenyl) nonane, R$_f$70 (2% ether-petroleum ether).

The 1-chloro-9-(p-[$^{125}$I]iodophenyl) nonane was next reacted with sodium (methylvaleryl) tellurol, as shown in step 6 above. To obtain sodium (methylvaleryl) tellurol, Na$_2$Te$_2$ (1.5 g, 5 mmol) was reacted with Br-(CH$_2$)$_4$-COOCH$_3$ (2.15 g, 11 mmol) to provide bis-(methylvaleryl) ditelluride, and the orange-colored ditelluride (48 mg, 0.1 mmol) was then reduced under argon at room temperature with excess NaBH$_4$ in ethanol (10 mL) to the colorless solution of the sodium (methylvaleryl) tellurol compound 6 above. As illustrated in the equation representing step 6 above, a solution of 1-chloro-9(p-[$^{125}$I]iodophenyl) nonane (4.6 mg) in 5 ml of ethanol was added dropwise to 5 ml of the solution of sodium (methlyvaleryl) tellurol prepared as indicated above. The resulting mixture was refluxed under argon for 1 hour, cooled in an ice bath, diluted with H$_2$O, and extracted three times with ether. The ether extracts were washed with H$_2$O, dried, and the solvent was removed in the usual manner. The product was chromatographed on a silicic acid column (basic grade, 2 cm I.D.). Fractions 24–27 were combined to give 1.1 mCi (80%) of methyl-15(p-[$^{125}$I]iodophenyl)-6-tellurapentadecanoate) compound 7 above. Upon TLC analysis, the produced showed a single radioactive component that co-chromatographed in C$_6$H$_6$ with unlabelled methyl-15(p-iodophenyl)-6-tellurapentadecanoate.

In step 7, the estermethyl-15(p-[$^{125}$I]iodophenyl)-6-tellurapentadecanoate (5.7 ml) was refluxed under argon for 30 minutes in ethanol (6 ml) containing 2 ml of 1 N NaOH (2 mmol). After cooling, the solution was diluted with H$_2$O, the pH adjusted to 2–4 with 10% H$_2$SO$_4$, and the resulting cloudy solution extracted several times with ether. After washing with H$_2$O and drying over anhydrous Na₂SO₄, the solvent was evaporated under argon to give 715 μmCi (65%) of 15-(p-[$^{125}$I]-iodophenyl)-6-tellurapentadecanoic acid, which showed a single radioactive component ($R_f$ 0.50) on TLC analysis (8% MeOH/CHCl₃). The specific activity of the product was 94 mCi/mmol.

The intermediate compound 1-chloro-9(p-iodophenyl) nonane (compound 5 above) was also prepared as follows. To a solution of 1-chloro-9[p[bis (trifluoroacetyl)thallium]phenyl]nonane (2.04 g, 3 mmol) in H₂O (30 mL) was added potassium iodide 3.00 g, 17 mmol), and the resulting cloudy solution was stirred at room temperature for 15 minutes. Sodium metabisulfite (1 g) was then added, and the mixture was stirred until the solution turned yellow. After being stirred 30 minutes, the solution was made basic with 1 N NaOH, filtered, and extracted thoroughly with ether. The combined ether extracts were washed with H₂O, dried over anhydrous Na₂SO₄, and evaporated in vacuo to afford a yellow residue. The residue was taken up in benzene (2 ml) and chromatographed to yield 0.64 g (64%) of 1-chloro-9(p-iodophenyl)nonane, compound 8 above.

In Table I, the tissue distribution of radioactivity in rats after intravenous administration of a bovine seriumalbumin complex of the 15-(p-[$^{125}$I]-iodophenyl)-6-Tellurapentadecanoic acid is summarized for various time periods from 5 minutes to 5 days. For comparison, the data for percent injected dose/organ are shown in Table II.

similar agents. After 6 hours the heart retained 80% of the maximum uptake observed after 5 minutes (Table I). The radioactivity in the heart retained 55% of the maximal value after 24 hours. The mean heart-to-blood ratios were 22:1 at 5 minutes and 17:1 at 2 hours. Only marginal radioactivity accumulated in the thyroid tissue; 1.52% dose/g after 5 minutes and 5.84% dose/g after 6 hours. The minimal thyroid radioactivity (Table I) and low blood levels demonstrate that the attachment of the radioiodine to the phenyl ring is an effective means of stabilizing the iodine and overcoming facile in vivo cleavage.

The rats used in the study were housed in metabolism cages and liquid and solid wastes were collected daily after injection of 15-(p-[$^{125}$I]-iodophenyl)-6-tellurapentadecanoic acid to determine the biological half-life of this new agent and its relative excretion in urine and feces. These studies were conducted over a five-day period, which represents a decay period of half-lives for 13.2-hr iodine-123. The cumulative excretion levels in urine and feces were 43.2±1.8% injected dose after two days and 71.6±8.3% after five days. The radioactive content of the urine (20.8±2.1%) and feces 22.4±1.1%) were similar after two days, but after five days the cumulative fecal activity (41.4±4.3%) was greater than that for urine (30.5±4.0%). The pronounced heart uptake, minimal deiodination, rapid blood clearance, and prolonged myocardial retention of 15-(p-[$^{125}$I]iodophenyl)-6-tellurapentadecanoic acid

TABLE I

DISTRIBUTION OF RADIOACTIVITY (% INJECTED DOSE/G OF TISSUE) IN RAT AT VARIOUS TIMES AFTER INTRAVENOUS ADMINISTRATION OF 15-(p-[$^{125}$I]IODOPHENYL)-6-TELLURAPENTADECANOIC ACID*

Time after Injection: Percent injected dose/g (range)

| Tissue | 5 min | 30 min | 60 min | 2 h | 6 h | 1 d | 5 d |
|---|---|---|---|---|---|---|---|
| Heart | 5.87 | 5.43 | 5.55 | 5.85 | 4.78 | 3.25 | 0.94 |
| | (5.30–6.45) | (4.35–5.98) | (4.01–7.27) | (4.01–7.56) | (3.89–5.33) | (3.02–3.41) | (0.77–1.13) |
| Blood | 0.26 | 0.45 | 0.34 | 0.42 | 0.31 | 0.20 | 0.03 |
| | (0.24–0.27) | (0.38–0.50) | (0.28–0.40) | (0.32–0.57) | (0.29–0.32) | (0.18–0.21) | (0.03–0.034) |
| Lungs | 1.14 | 1.25 | 1.48 | 1.57 | 1.10 | 0.89 | 0.33 |
| | (0.86–1.52) | (1.14–1.40) | (1.10–1.95) | (1.29–2.05) | (0.97–1.17) | (0.77–1.05) | (0.30–0.36) |
| Liver | 9.57 | 7.78 | 7.69 | 8.38 | 8.37 | 6.24 | 1.28 |
| | (8.97–10.28) | (6.73–8.86) | (6.68–8.28) | (7.32–9.90) | (7.86–9.08) | (5.53–6.73) | (1.23–1.36) |
| Kidneys | 1.02 | 1.25 | 1.41 | 1.37 | 1.12 | 0.70 | 0.20 |
| | (0.79–1.15) | (1.09–1.39) | (1.23–1.55) | (1.20–1.69) | (0.95–1.20) | (0.63–0.80) | (0.18–0.22) |
| Thyroid | 1.52 | 1.51 | 1.48 | 3.51 | 5.89 | 22.78 | 30.25 |
| | (1.41–1.63) | (0.83–2.21) | (0.95–1.94) | (1.91–4.42) | (5.33–7.08) | (18.15–27.13) | (25.26–34.81) |

TABLE II

DISTRIBUTION OF RADIOACTIVITY (% INJECTED DOSE/ORGAN) OF RADIOACTIVITY IN RAT AT VARIOUS TIMES AFTER INTRAVENOUS ADMINISTRATION OF 15-(p-[$^{125}$I]IODOPHENYL)-6-TELLURAPENTADECANOIC ACID*

Time after Injection: Percent injected dose/organ (range)

| Tissue | 5 min | 30 min | 60 min | 2 h | 6 h | 1 d | 5 d |
|---|---|---|---|---|---|---|---|
| Heart | 2.98 | 2.61 | 2.87 | 2.87 | 2.32 | 1.60 | 0.45 |
| | (2.80–3.35) | (2.19–2.91) | (2.09–3.80) | (2.60–3.48) | (1.66–2.65) | (1.40–1.73) | (0.38–0.52) |
| Blood | 2.00 | 3.41 | 2.66 | 3.01 | 2.26 | 1.50 | 0.23 |
| | (1.89–2.09) | (2.65–3.93) | (2.24–3.24) | (2.33–3.99) | (2.23–2.31) | (1.37–1.62) | (0.22–0.25) |
| Lungs | 0.97 | 1.05 | 1.01 | 1.29 | 0.85 | 0.70 | 0.24 |
| | (0.74–1.30) | (0.97–1.04) | (0.85–1.16) | (1.12–1.67) | (0.73–0.94) | (0.58–0.85) | (0.22–0.26) |
| Liver | 50.94 | 39.28 | 39.03 | 44.03 | 46.39 | 34.28 | 6.46 |
| | (46.13–55.20) | (34.11–43.16) | (34.62–41.81) | (41.59–47.61) | (43.86–49.26) | (32.02–37.42) | (6.00–6.84) |
| Kidneys | 1.25 | 1.52 | 1.73 | 1.53 | 1.25 | 0.81 | 0.23 |
| | (0.95–1.44) | (1.42–1.63) | (1.47–1.97) | (1.37–1.80) | (1.09–1.38) | (0.74–0.87) | (0.21–0.27) |
| Thyroid | 0.02 | 0.02 | 0.02 | 0.04 | 0.07 | 0.26 | 0.32 |
| | (0.02–0.02) | (0.01–0.02) | (0.01–0.02) | (0.02–0.05) | (0.06–0.09) | (0.22–0.30) | (0.28–0.35) |

The rapid and pronounced myocardial uptake observed with the disclosed imaging agent in analogous to that reported for 9-[$^{123m}$Te]-HDA. Prolonged retention of radioactivity is exhibited by the 15-(p-[$^{125}$I]iodophenyl)-6-tellurapentadecanoic acid, and studies have indicated that its p-iodophenyl moiety does not interefere with the myocardial specificity observed with similar agents suggest that the $^{123}$I-labeled analog is also an attractive agent with which to evaluate myocardial perfusion.

What is claimed is:

1. The compound 15-(p-[$^{125}$I]-iodophenyl-6-tellurapentadecanoic acid.

* * * * *